(12) United States Patent
Collier

(10) Patent No.: US 6,220,083 B1
(45) Date of Patent: Apr. 24, 2001

(54) ELONGATIONAL RHEOMETER AND ON-LINE PROCESS CONTROLLER

(75) Inventor: John R. Collier, Baton Rouge, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 09/172,056

(22) Filed: Oct. 14, 1998

Related U.S. Application Data
(60) Provisional application No. 60/198,256, filed on Oct. 17, 1997.

(51) Int. Cl.[7] .............................. G01N 11/04; G01N 11/08
(52) U.S. Cl. ............................................................ 73/54.14
(58) Field of Search ................................. 73/54.11, 54.14

(56) References Cited

U.S. PATENT DOCUMENTS

| | | |
|---|---|---|
| 2,538,785 | 1/1951 | Karig . |
| 3,017,767 | 1/1962 | Mossberg . |
| 3,203,225 | 8/1965 | Sieglaff et al. . |
| 3,252,320 | 5/1966 | Welty . |
| 3,270,553 | 9/1966 | Ballman et al. . |
| 3,678,733 | 7/1972 | Blatter . |
| 4,241,602 | 12/1980 | Han et al. . |
| 4,316,383 | 2/1982 | Fruman et al. . |
| 4,624,132 | * 11/1986 | Parnaby et al. ..................... 73/53.09 |
| 4,680,958 | 7/1987 | Ruelle et al. . |
| 5,202,395 | * 4/1993 | Chambon ............................. 73/54.14 |
| 5,277,058 | 1/1994 | Kalyon et al. ...................... 73/54.11 |
| 5,357,784 | 10/1994 | Collier ................................. 73/54.14 |
| 5,583,284 | 12/1996 | Martin et al. . |

OTHER PUBLICATIONS

Andrew, W., *Applied Instrumentation in the Process Industries*, vol. 1, pp. 234–236 (1974).
Bersted, B., "Refinement of the Converging Flow Method of Measuring Extensional Viscosity in Polymers," *Polym. Eng. and Sci.*, vol. 33, pp. 1079–1083 (1993).
Binding, D. et al., "On the interpretation of data from converging flow rheometers," *Rheol. Acta*, vol. 28, pp. 215–222 (1989).
Chatraei, S. et al., "Lubricated Squeezing Flow: A New–Biaxial Extensional Rheometer," *J. Rheol.*, vol. 25, No. 4, pp. 433–443 (1981).
Cogswell, F., "Measuring the Extensional Rheology of Polymer Melts," *Trans. Soc. Rheol.*, vol. 16, pp. 383–403 (1972).
Crevecoeur, G. et al., "Fibril Formation in In situ Composites of a Thermotropic Liquid Crystalline Polymer in a Thermoplastic Matrix," *J. App. Pol. Sci.*, vol. 49, pp. 839–849 (1993).
James, D., "Flow in a Converging Channel at Moderate Reynolds Numbers," *A.I.Ch.E.J.*, vol. 37, No. 1, pp. 59–64 (1991).
Jones, D., "On the extensional viscosity of mobile polymer solutions," *Rheol. Acta*, vol. 26, pp. 20–30 (1987).
Kwag, C., "An Assessment of Cogswell's Method for Measurement of Extensional Viscosity," *Polym. Eng. and Sci.*, vol. 31, pp. 1015–1021 (1991).

(List continued on next page.)

*Primary Examiner*—Daniel S. Larkin
(74) *Attorney, Agent, or Firm*—John H. Runnels

(57) ABSTRACT

Elongational viscosity may be easily and accurately measured by observing the flow characteristics of a high viscosity fluid through a hyperbolic or semi-hyperbolic die, without lubrication of the fluid flowing through the die. The effects of developing orientation in the fluid during converging elongational flow are so strong that the shearing contribution becomes negligible in comparison, eliminating the need for lubrication during measurements.

4 Claims, 1 Drawing Sheet

OTHER PUBLICATIONS

Meissner, J., "Dehnungsverhalten von Polyäthylen–Schmelzen," *Rheol. Acta*, vol. 10, No. 2, pp. 230–242 (1971).

Meissner, J., "Development of a Universal Extensional Rheometer for the Uniaxial Extension of Polymer Melts," *Trans. Soc. Rheol.*, vol. 16, pp. 405–420 (1972).

Meissner, J., "Rheometer zur Untersuchung der deformationsmechanischen Eigenschaften von Kunstoff–Schmelzen unter definierter Zugbeanspruchung," *Rheol. Acta*, vol. 8, No. 1, pp. 78–88 (1969).

Revenu, P. et al., "Validation of Cogswell's Convergent Flow Analysis," *J. Appl. Polym. Sci.*, vol. 62, pp. 1783–1792 (1996).

Rheometrics data sheet, "RME—Rheometrics elongational rheometer for melts" (1993).

Simionescu, C. et al., "Romanian Wood Chemistry," RSR Academy Publishing House, Bucharest (1973) [Single-page excerpt, Eng. translation].

Williams, P. et al., "On the Planar Extensional Viscosity of Mobile Liquids," *J. Non–Newtonian Fluid Mechanics*, vol. 19, pp. 53–80 (1985).

Zahorski, S., "The converging flow rheometer reconsidered: an example of flow with dominating extension," *J. Non–Newtonian Fluid Mech.*, vol. 41, pp. 309–322 (1992).

* cited by examiner

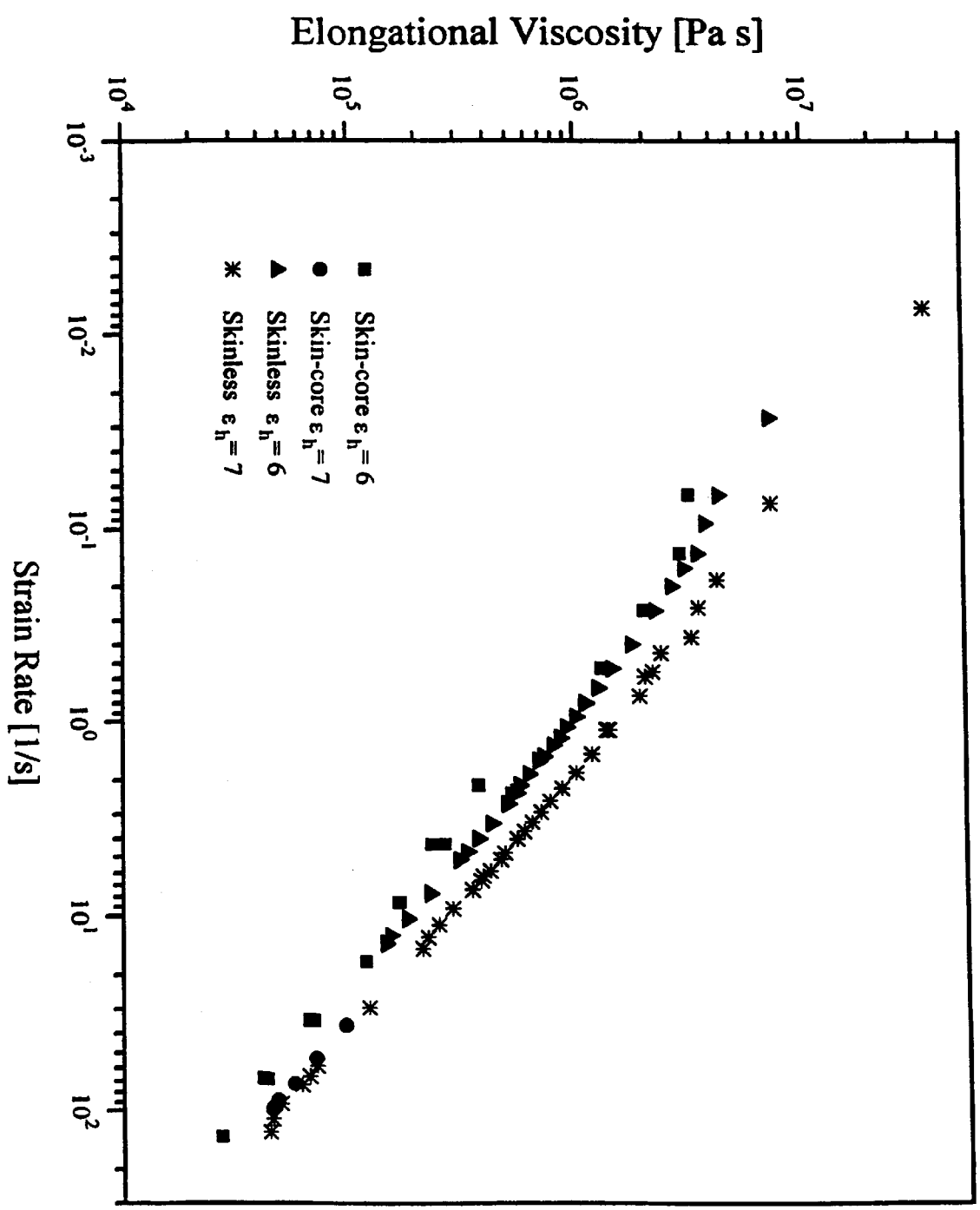

ELONGATIONAL RHEOMETER AND ON-LINE PROCESS CONTROLLER

The benefit of the Oct. 17, 1997 filing date of provisional application 60/198,256 (which was a conversion of nonprovisional application 08/953,179) is claimed under 35 U.S.C. § 119(e).

This invention pertains to rheometry, particular to a method and instrument for measuring elongational viscosity, and to apparatus and methods for using those measurements in on-line process control.

Rheology is the study of the deformations and flow of matter. A rheometer is a device for measuring the flow of a viscoelastic substance, usually a fluid, for example a polymer melt or solution. The viscosity of a complex substance may be characterized (depending on the geometry of the flow) by its shear viscosity, its elongational viscosity, or a combination of shear and elongational viscosities. Shear viscosity is the resistance to flow due to a force that is perpendicular to the normal of the plane on which the force acts (i.e., a force lying in the surface of flow). Elongational viscosity is the resistance to flow due to a force that is parallel to the normal of the plane on which the force acts. The shear viscosity may be thought of, for example, as the resistance to fluid flow between layers; and the elongational or extensional viscosity may be thought of as the resistance of the fluid to stretching. As a general rule, there is little correlation between shear viscosity and elongational viscosity for complex substances. Knowledge of one does not, in general, allow prediction of the other with any degree of confidence. (For simple or Newtonian fluids, the ratio of the elongational viscosity to the shear viscosity is determined by the geometry of the flow; e.g., in cylindrical flow this ratio is 3. However, polymer solutions and melts do not, in general, behave as Newtonian fluids, and there is no simple relation between shear and elongational viscosities.)

Shear rheometry, the measurement of shear viscosity, is a well-developed field. Most current rheometers measure shearing flow. By contrast, extensional or elongational rheometry is still in its formative stages. It is becoming increasingly apparent that extensional flow is important in many industrial applications, including fiber spinning; film casting; extrusion; and the fountain flow of the filling front during injection molding, where the primary flow field is extensional. There is a continuing need for improved methods for the accurate measurement of the extensional viscosity of fluids under operating conditions.

Compared to shear rheometry, the main difficulties in studying the extensional flow of viscoelastic fluids are that (1) it is difficult to generate a steady and controlled elongational flow field, and (2) it has been thought difficult to prevent, compensate, or even measure the shear effects that typically occur simultaneously during elongational flow.

Zahorski, "The Converging Flow Rheometer Reconsidered: An Example of Flow with Dominating Extension," *J. Non-Newtonian Fluid Mech.*, vol. 41, pp. 309–322 (1992) discusses theoretical predictions concerning two-dimensional planar extrusion in a lubricated converging flow rheometer; no experimental data are given. Zahorski states that the flow cannot be expected to be purely extensional—measurable shear effects were said to be certain.

Chatraei et al., "Lubricated Squeezing Flow: A New Biaxial Extensional Rheometer," *J. Rheol.*, vol. 25, no. 4, pp. 433–443 (1981) discloses a lubricated biaxial flow apparatus for measuring elongational viscosity in which a viscous material is compressed between two lubricated disks; no means are disclosed for achieving a constant elongational strain rate.

Williams et al., "On the Planar Extensional Viscosity of Mobile Liquids," *J. Non-Newtonian Fluid Mechanics*, vol. 19, pp. 53–80 (1985) discloses an instrument for measuring planar extensional viscosity with lubricated converging flow in a hyperbolic planar nozzle. Such a device would primarily be useful for measuring the viscosity of solutions or other relatively low viscosity fluids. The apparatus would not be practical for measurements in high viscosity fluids such as many polymer melts, because it would be difficult to achieve a steady flow of such fluids in the planar nozzle. See also Binding et al., "On the interpretation of data from converging flow rheometers," *Rheol. Acta*, vol. 28, pp. 215–222 (1989); Jones, "On the extensional viscosity of mobile polymer solutions," Rheol. Acta, vol. 26, pp. 20–30 (1987); and James, "Flow in a Converging Channel at Moderate Reynolds Numbers," *A.I. Ch.E.J.*, vol. 37, no. 1, pp. 59–64 (1991).

Rheometrics data sheet, "RME—Rheometrics elongational rheometer for melts" (1993) describes a system for measuring the elongational viscosity of a fluid in which the fluid is supported by a gas stream, and the ends are pulled apart by traction at an exponentially increasing speed; the disclosures of the following two references are similar to that of the Rheometrics data sheet in many respects, except that the fluid was floated on oil rather than supported by a gas stream: Meissner, "Rheometer zur Untersuchung der deformationsmechanischen Eigenschaften von Kunstoff-Schmelzen unter definierter Zugbeanspruchung," *Rheol. Acta*, vol. 8, no. 1, pp. 78–88 (1969); and Meissner, "Dehnungsverhalten von Polyäthylen-Schmelzen," Rheol. Acta, vol. 10, no. 2, pp. 230–242 (1971).

Crevecoeur et al., "Fibril Formation in InStu Composites of a Thermotropic Liquid Crystalline Polymer in a Thermoplastic Matrix," *J. App. Pol. Sci.*, vol. 49, pp. 839–849 (1993) discloses a trumpet-shaped die for measuring elongational viscosity in polymer melts containing fibers.

F. Cogswell, "Converging Flow of Polymer Melts in Extrusion Dies," *Polym. Eng. Sci.*, vol. 12, pp. 64–73 (1972); and F. Cogswell, "Measuring the Extensional Rheology of Polymer Melts," *Trans. Soc. Rheol.* vol. 16, pp. 383–403 (1972) provide estimates for elongational and shearing viscosity derived from measurements with a capillary rheometer, based on assumptions that may not adequately model actual conditions of polymer flow, for example, the assumption that there is only a low pressure loss when a fluid flows from a large section to a small one.

See also J. Meissner, "Development of a Universal Extensional Rheometer for the Uniaxial Extension of Polymer Melts," *Trans. Soc. Rheol.*, vol. 16, pp. 405–420 (1972); C. Kwag, "An Assessment of Cogswell's Method for Measurement of Extensional Viscosity," *Polym. Eng. and Sci.*, vol. 31, pp. 1015–1021 (1991); W. Andrew, *Applied Instrumentation in the Process Industries*, vol. 1, pp. 234–236 (1974); B. Bersted, "Refinement of the Converging Flow Method of Measuring Extensional Viscosity in Polymers," *Polym. Eng. and Sci.*, vol. 33, pp. 1079–1083 (1993); P. Revenu et al., "Validation of Cogswell's Convergent Flow Analysis," *J. Appl. Polym. Sci.*, vol. 62, pp. 1783–1792 (1996); and D. Cousidine (ed.), *Process Instruments and Controls Handbook*, pp. 11.3–11.25 (1985).

The present inventor's prior U.S. Pat. No. 5,357,784 discloses a method and apparatus for measuring the elongational viscosity of a fluid, in which a low viscosity fluid "skin" encapsulates and lubricates a viscous core of the fluid being characterized. A high viscosity material, such as a polymer melt, is caused to flow at a controlled constant strain rate in an essentially pure elongational flow regime, for example inside a die, by using lubricated flow and a semi-hyperbolic surface design. Lubricated flow results from skin/core flow, in which the viscosity of the skin is sufficiently lower than that of the core to cause the core to experience essentially pure elongational flow. With a semi-hyperbolic surface, essentially pure elongational flow can be maintained at a steady-state, controlled, constant elongational strain rate. The apparatus and method of prior U.S. Pat. No. 5,357,784 are well suited for the uses taught in that patent. However, prior U.S. Pat. No. 5,357,784 taught that the flow must be lubricated in order to measure elongational viscosity accurately; i.e., that a lubricating skin layer was needed due to the effect of the shearing gradients associated with a rigid boundary. Although the technique of the prior patent has been successful, in many applications it is inconvenient or impractical to apply a lubricating skin layer.

Current on-line process control schemes for polymer processing typically use only shearing rheology measurements, and therefore do not provide a reasonable indication of the orienting ability of the polymer melt or solution.

Surprisingly, it has now been discovered that elongational viscosity may be easily and accurately measured by observing the flow characteristics of a high viscosity fluid through a semi-hyperbolic die, without lubrication of the fluid flowing through the die. It has been unexpectedly discovered that the effects of developing orientation in the fluid during converging elongational flow are so strong that the shearing contribution becomes negligible in comparison, eliminating the need for lubrication during measurements.

Before the developments disclosed here, it was generally accepted that elongational data from skinless measurements required correction to compensate for the lack of a lower viscosity lubricating layer. Without a lubricating skin layer, it would previously have been expected that the shear gradient near the die wall would increase the pressure drop required for a given flow rate as compared to the flow rate of otherwise comparable lubricated flow. It has unexpectedly been found that no such correction is necessary, and that in a converging flow regime lubricated and skinless elongational measurements are nearly identical for most practical purposes. The reason for this surprising conclusion is the unexpected finding that the flow of non-Newtonian visco-elastic fluids (which includes but is not limited to polymer melts and all but very low concentration polymer solutions) is dominated by the fluid's resistance to orientation, with the fluid transforming from an isotropic liquid to an ordered liquid or liquid crystal. The momentum balance is dominated by a body force related to this orientation development. An enthalpy change accompanies the orientation development.

A fluid in a liquid crystalline state has regions or domains of one or two dimensional order that are generally larger than the individual flow units; however until deformation (i.e. flow) or another external force (e.g. temperature or concentration gradient) is imposed, these domains are randomly arranged with respect to one another. The resistance to orientation is due to alignment of the domains, and alignment of the molecules inside domains. If a fluid is not in a liquid crystalline state when an elongational deforming force is applied, the resulting flow causes the material to begin to orient, causing it to enter a metastable (or perhaps even a stable) liquid crystalline state. If the orientation is highly ordered, then the metastable form becomes a well-ordered liquid crystal with a preferred order in one or two directions. If the orientation is not highly ordered, then the metastable form is a poorly organized liquid crystal. Depending on the composition of the fluid and the conditions of flow, the order imposed by flow may be partially or completely lost by fluid relaxation after exiting the converging flow, unless it is retained by inducing a phase change as disclosed here. Although the flow-induced phase change may be reversible thermodynamically, the kinetics of re-dissolving in some systems may be slow compared to the time of cooling. The rate of change in a phase transformation under the influence of the flow increases, since the kinetics of phase change in polymeric systems are greatly affected by the difficulty of aligning long chain molecules over a sufficient length to be stable. A second resistance to transformation to a solid crystalline form is rotation of portions of the molecules to adopt three dimensional order. Since in elongational flow the alignment of polymer chains is imposed mechanically (i.e. by the flow), the major resistance to the phase change is eliminated or significantly reduced. It is not necessary for the fluid to be in a liquid crystalline state, although such a state is beneficial.

Elongational strain imparts orientation to a polymer, a property that is significant not only when a particular process is intended to impart controlled levels of orientation (e.g. fiber spinning, film blowing, film tentering (orienting a sheet or film by pulling), bottle blowing), but also in other operations where "inadvertent" orientation of polymer molecules may affect the properties of fabricated products (e.g. those produced by injection molding and extrusion). The skinless measurement capability makes elongational viscosity measurements considerably more practical and attractive.

The novel process may be used for measurement of rheological properties, alone or as part of an on-line process controller, in which elongational viscosities (optionally in conjunction with other properties) are measured in real time or pseudo-real time as part of a feedback loop that is used to control a process, such as polymer manufacture, fabrication, or extrusion. The orienting ability of a polymer melt or solution may now be monitored by measuring both elongational and shearing rheological measurements together Better measurement of the orientability of polymer melts and polymer solutions, and the retention of that orientation, coupled with measurements of viscous shearing flow behavior, will enable better control of such processes as fiber spinning, film blowing and tentering, bottle blowing, injection molding, and extrusion. The affinity to orient, and the retention of orientation is important in many polymer processing operations, but these properties are only slightly, and often inaccurately, indicated by measurements of shearing viscosity alone.

Existing on-line process controllers often have a shearing viscosity sensing capability, and they often also have a bypass line integrated into the unit. An existing bypass line may be replaced with the novel converging rheometer; if a bypass line does not exist, then an additional line or a series line and appropriate valving may be added. Existing pressure and flow sensors may be used to characterize flow through the rheometer line. The added ability to measure elongational viscosity on-line enhances the operator's ability to monitor and control polymer properties. Shearing rheological properties reflect the influence of flow past fixed boundaries. However, shearing measurements predict polymer orientability and orientation retention poorly at best. Because most polymer processing operations and many polymer applications either depend upon, or are significantly affected by, orientability and retention of orientation, the novel approach to measuring elongational viscosity will be useful in many applications.

Orientation of polymer molecules is desirable in applications, such as fiber spinning, film blowing and tentering, and blow molding. However, the development and retention of orientation may be detrimental in other applications, such as injection molding and profile extrusion. Whether orientation is desirable or undesirable in a particular application, the novel technique allows the orientation properties to be monitored and controlled as desired.

For example, in fiber spinning elongational viscosity affects drawability, the resistance to deformation, and the retention of orientation. A reduction in elongational viscosity can produce lowered orientation in the fibers, without significant changes in the processing conditions. Monitoring the elongational viscosity allows real-time process changes to compensate. For example, compensations for a drop in elongational viscosity might include a decrease in temperature in order to increase the melt or solution viscosity, or an increase in the draw rate. In another example, injection molding, an increase in elongational viscosity can increase residual stress after molding; the residual stress can lead to excessive stress relaxation and dimensional changes in the molded object. Possible on-line compensations for an increased elongational viscosity include increasing the melt temperature, increasing the mold temperature, and increasing the cooling time.

BRIEF DESCRIPTION OF THE DRAWING

The FIGURE compares elongational viscosity measurements made with and without a lubricating low-viscosity skin layer.

A converging geometry is used to impose a constant elongational strain rate, $\epsilon$, on the fluid. The value of the elongational strain rate is determined both by the die geometry and by the volumetric flow rate. Two particular converging geometries have been used in embodiments to date, although the invention is not limited to these embodiments: a hyperbolic slit and a semi-hyperbolic cone. The slit geometry was used primarily to validate the basic principles of the rheometer. In the slit geometry, various hyperbolically converging inserts could be placed into an available die with glass side windows. This configuration permitted optical observation of tracer particles, to confirm velocity profiles in the fluid.

A "semi-hyperbolic" surface is defined as one in which, for a suitable choice of origin, Az is constant or $R^2z$ is a constant, where z denotes the displacement along the direction of flow, A is the cross-sectional area of the interior of the surface in a plane normal to the direction of flow, and R is the radius of the interior of the surface in a plane normal to the direction of flow in the preferred case where the cross-section is circular. Put differently, in the direction of the z-axis (the direction of fluid flow), the cross-sectional area decreases as z increases, with the area being proportional to 1/z. Such a surface may be generated, for example, by rotating about the z-axis the curve $R=(C_1/z)^{1/2}$, where $C_1$ is a constant.

The present invention is compatible with many existing capillary shear rheometers, so that extensive retrofitting is not required to practice the invention in conjunction with such rheometers. For example, an auxiliary unit including a conical, semi-hyperbolic die in accordance with the present invention may be added to an existing capillary melt rheometer without needing extensive additional apparatus. An accessory for conventional capillary rheometers could readily be made that would allow the novel elongational rheometer of this invention to be used in conjunction with the normal shearing flow measurements made by the capillary system. A capillary rheometer accessory would preferably have the conical shape of a rotated (or "conical") semi-hyperboloid.

The novel system is flexible. Any of a wide range of constant strain rates may be selected by switching semi-hyperbolic (or hyperbolic) die (or die inserts) of appropriate profile, or by varying the volumetric flow rate.

It is desirable that the flow have a constant elongational strain rate in at least a portion of the measurement section, a result readily achieved, for example, with a semi-hyperbolic-shaped converging section. The elongational strain rate may be controlled by the varying the mass flow rate. This invention is particularly useful in process control as an on-line rheometer, operating either continuously or in a batch mode, on a side stream from an industrial melt or other flow. For a discussion of on-line process control generally, see Chapter 2 of D. J. Huskins, *Quality Measuring Instruments in on-line process analysis*, Ellis Horwood Series in Analytical Chemistry (1982). For example, page 119 of this reference discloses an on-line capillary shear viscometer. That viscometer could include a side stream containing a gear pump followed by a capillary. The gear pump forces the fluid to have a nearly constant volumetric flow. Pressure is determined by conditions at the entrance and exit of the capillary (for example, whether exiting flow is into atmospheric pressure or back into the main process flow channel). Alternatively, the power input to or torque upon the drive motor of the gear pump could be used as a proxy measure of the pressure drop. In some applications it will be desirable to use two capillaries with proper valving, one a conventional cylinder for shear measurements, and the other a converging cylinder as disclosed here for elongational measurements.

Those of skill in the art will recognize that the converging section of the die could be designed with a shape other than a strictly conical semi-hyperbolic shape (i.e., having a circular cross section), so long as the cross-sectional area in the converging section converged at the same rate. For example, in the planar case one side could be hyperbolic, and the other side flat; the distance between the sides still decreases hyperbolically. Or a sine-wave could be added to one face, and subtracted from the other. In the axially symmetric case, instead of a rotated semi-hyperboloid, one might use half of such a semi-hyperboloid, in which a flat plane including the axis of symmetry cuts the semi-hyperboloid in two. Another alternative, in which biaxial flow is measured, is flow in a cylinder past a mandril, where both the cylinder and the mandril have semi-hyperbolic shapes converging towards one another, and the flow is in the direction away from the "neck" of the semi-hyperboloids. This may be visualized as similar in some sense to the flow of air through a muted trumpet. Other examples of such alternatives will readily occur to one of skill in the art. In all these cases and others satisfying the definition given above for a semi-hyperbolic shape, the flow velocity increases linearly with length in the direction of the flow, and the cross-sectional area decreases proportionately.

Furthermore, strict adherence to a semi-hyperbolic shape may not be needed due to the surprising strength of the orientation effect, and the tendency of viscoelastic materials to define their own convergence patterns by developing recirculation patterns in converging flow channels. In some applications, it will suffice to have a proxy (i.e., indicative of approximate) measurement of orientability. A die with a generally regular (but not necessarily constant) convergence should yield a useful proxy measurement of orientability. The Hencky strain in such a case should preferably be ~2 or greater, and the ratio of the die's length to the diameter should preferably be ~2 or greater, particularly to prevent flow behavior at the entrance from predominating. Even these conditions need not always be satisfied, as viscoelastic fluids tend to define a wine-glass type entrance flow at a constriction.

In a simple alternative embodiment, a gear pump is placed in a side stream of the polymer melt or solution, followed by flow into a channel with a diameter comparable to that of the gear pump discharge, followed in turn by a sudden contraction to flow through a capillary of a significantly smaller cross-section. By measuring the pressure at gear pump discharge, at the capillary entrance (not upstream from the entrance due to the vortices immediately adjacent to the entrance), and at capillary exit (which could be atmospheric pressure not requiring separate measurement if the sample does not reenter the main flow stream), one may obtain a proxy measure of the elongational and shearing viscosities. The volumetric flow rate is controlled by the gear pump, the pressure drop for estimating elongational viscosity is the difference between the pressure at exit of the gear pump and the pressure at the entrance to the confined flow, and the pressure drop for estimating the shearing viscosity is the difference between the pressure at the capillary entrance and the pressure at the capillary exit. Preferably, additional pressure measurements are also made, and a defined converging flow channel is placed between the gear pump and the capillary (i.e. a geometry machined into the die wall). Because the entrance effects occur right at the entrance to the constricted flow, the length of the flow channel between the gear pump exit and the constricted flow need not be long. By using a shaped (preferably semi-hyperbolic) convergence, a better measurement may be made of the elongational effect, by avoiding the pressure drops that are associated with recirculation vortices in a "wine-glass stem" geometry.

A different shape of die, which will also measure biaxial flow at a constant elongational strain rate along both axes, is one in which the flow converges hyperbolically along the x-axis as the fluid flows in the direction of the z-axis, while simultaneously diverging hyperbolically along the y-axis.

As used in the specification and claims, the term "die" is not intended to have any special meaning; rather, "die" is intended to refer to a portion of the measuring apparatus that causes converging flow of the fluid, particularly converging flow through a semi-hyperbolic shape.

The elongational viscosity may be expressed as $$\eta_{ef} = a\left(\frac{\Delta P A_{ex} L}{Q \epsilon_h}\right) - b = a\left(\frac{\Delta P L}{v_o \epsilon_h \exp(\epsilon_h)}\right) - b$$

wherein the Hencky strain, $\epsilon_h$, is natural logarithm of the ratio of the entrance area to the exit area in the die. The values of the parameters a and b are determined by the shape of the die. For well defined hyperbolic dies, with a Hencky strain large enough to have stable flow ($\epsilon_h$ greater than about 4) the values of a and b are approximately 1 and 0, respectively L is the centerline length of the converging section, $A_{ex}$ is the cross sectional area of the channel as the fluid exits the converging section, $\Delta P$ is the pressure drop of the fluid in the converging section, Q is the volumetric flow rate, and $v_o$ is the entrance velocity.

Theoretical Considerations

Without wishing to be bound by the following theory, the following discussion presents the theory that is believed to underlie the formation of microfibers in the novel process. Unless otherwise indicated, this theoretical analysis applies both to skinless flow and to the core material in skin/core lubricated flow conditions. The distinction between skinless flow and the core of skin/core flow is more important in elongational rheological measurements, but is also pertinent to the formation of microfibers.

Because the skin layer has a viscosity substantially lower than the viscosity of the core, the shearing gradient from the die wall is essentially confined to the skin, producing an essentially elongational flow pattern in the core.

In a preferred embodiment, the die's convergence geometry is chosen to force a constant elongational strain rate, $\dot{\epsilon}$, in the core. Although other die geometries are possible, two preferred geometries, the geometries that have been used in prototype experiments, are the hyperbolic slit and the semi-hyperbolic cone. A hyperbolic die is one for which a longitudinal line reflected onto the surface would trace out a hyperbola. In what is referred to as a "semi-hyperbolic cone" the relationship between the radius of the cone's inside surface, R, and the longitudinal direction, z, is $R^2 z = C_1$, where $C_1$ is a constant. A hyperbolic slit has a constant width, W, along the y-axis, and its width measured along the x-axis is given by $Xz=C_2$, where $C_2$ is a constant. For the hyperbolic slit, the semi-hyperbolic cone, and other "semi-hyperbolic" surfaces, the area perpendicular to the centerline of flow is directly proportional to the reciprocal of the centerline distance from an origin, i.e. the cross-sectional area of flow is inversely proportional to the centerline distance. The semi-hyperbolic cone is preferred. The hyperbolic slit used in a prototype had a specially milled die insert, while the semi-hyperbolic cone used an ACER capillary rheometer with an electrodischarge-machined, semi-hyperbolically-converging capillary to replace the rheometer's normal capillary. Pressure drops and volumetric flow rates were measured in all cases.

The die shapes were chosen so that the interface between the polymer melt or solution and the die wall was a stream tube, i.e. a set of streamlines forming a two dimensional surface, with each streamline in that surface experiencing the same conditions, and having the same value of the stream function $\Psi$. The stream function must satisfy the continuity equation. The potential function, $\Phi$, must be orthogonal to $\Psi$ and satisfy the irrotationality equation. Constant values of the potential function define surfaces of constant driving force, i.e. constant pressure surfaces. As shown below semi-hyperbolic stream functions (and potential functions) satisfy these conditions for both the converging slit and converging cone geometries.

Hyperbolic Slit

For the hyperbolic slit in Cartesian coordinates the stream function and potential functions are respectively:

$$\Psi = -\dot{\epsilon} x z$$

$$\Phi = \frac{\dot{\epsilon}}{2}(x^2 - z^2)$$

The Cauchy-Riemann conditions and velocity gradients are:

$$v_z = -\frac{\partial \Psi}{\partial x} = -\frac{\partial \Phi}{\partial z}, v_x = \frac{\partial \Psi}{\partial z} = -\frac{\partial \Phi}{\partial x}$$

The non-zero velocity gradients are:

$$\frac{\partial v_z}{\partial z} = \dot{\varepsilon}, \frac{\partial v_x}{\partial x} = -\dot{\varepsilon}$$

Semi-hyperbolic cone

For the semi-hyperbolic cone in Cartesian coordinates, the stream function and potential functions are respectively:

$$\Psi = -\frac{\dot{\varepsilon}}{2}r^2 z$$

$$\Phi = \dot{\varepsilon}\left(\frac{r^2}{4} - \frac{z^2}{2}\right)$$

The Cauchy-Riemann conditions and velocity gradients are:

$$v_z = -\frac{1}{r}\frac{\partial \Psi}{\partial r} = -\frac{\partial \Phi}{\partial z}, v_r = \frac{1}{r}\frac{\partial \Psi}{\partial z} = -\frac{\partial \Phi}{\partial r}$$

The non-zero velocity gradients are:

$$\frac{\partial v_z}{\partial z} = \dot{\varepsilon}, \frac{1}{r}\frac{\partial (r v_r)}{\partial r} = -\dot{\varepsilon}$$

The basic equations describing the flow are the scalar equations of continuity (i.e., mass balance) and a form of energy balance expressed in terms of enthalpy per unit mass, Ĥ; and the first order tensor (i.e. vector) momentum balance. Mass, momentum, and energy are each conserved. These relations expressed in tensor notation are:

$$\frac{D\rho}{Dt} = -\rho(\nabla \cdot v) \text{ Continuity (Mass Balance)}$$

$$\rho\frac{D}{Dt}v = -(\nabla p) - [\nabla \cdot \tau] + \rho g \text{ Momentum Balance}$$

$$\rho\frac{D}{Dt}(\hat{H}) = -(\nabla \cdot q) - (\tau : \nabla v) - \frac{DP}{Dt} \text{ Energy Balance}$$

where τ, a second order tensor, denotes the stress, and the first order tensor (i.e. vector) quantities v and q denote velocity and energy flux, respectively. The body force term, g, is discussed in greater detail below; it is a first order tensor, which was found to represent primarily the force necessary to orient the material; this term would also include a gravitational component if the latter were significant. The first order tensor operator ∇ denotes the gradient. The scalar terms P, ρ, and Ĥ are the pressure, density, and enthalpy per unit mass, respectively.

The geometry of the hyperbolic and semi-hyperbolic dies used in prototype embodiments were chosen to cause the elongational strain rate ($\dot{\varepsilon}$) to be a constant whose value is determined by the geometry and the volumetric flow rate. The only velocity gradients encountered in essentially pure elongational flow are in the flow and transverse directions. Therefore the only non-zero components of the deformation rate second order tensor Δ are the normal components. If the fluid is assumed to be incompressible, then ∇·v=0. Thus the components of Δ are, expressed in both Cartesian and cylindrical coordinates:

$$\Delta_{ij} = \left(\frac{\partial v_i}{\partial x_j} + \frac{\partial v_j}{\partial x_i}\right), \text{ and } \Delta_{\theta\theta} = 2\left(\frac{1}{r}\frac{\partial v_\theta}{\partial \theta} + \frac{v_r}{r}\right).$$

In Cartesian coordinates the only non-zero components are the flow and transverse components, $\nabla_{zz}$ and $\nabla_{xx}$, respectively: $\nabla_{zz} = -\nabla_{xx} = 2\dot{\varepsilon}$.

The corresponding non-zero components in cylindrical coordinates are $\nabla_{zz}$, $\nabla_{rr}$, and $\nabla_{\theta\theta}$; where $\nabla_{zz}$ is the flow direction; $\Delta_{zz} = -2\Delta_{\theta\theta} = 2\dot{\varepsilon}$. (Note that $\nabla_{\theta\theta}$ and the corresponding stress tensor component $\tau_{\theta\theta}$ are both non-zero.)

Assumptions made in this theoretical analysis, along with some implications of these assumptions, include the following. (Note that these and other assumptions in this theoretical section, which were made for purposes of simplifying the theoretical analysis, need not be rigorously satisfied in practical applications.)

1. The stress state in a fluid is uniquely determined by its strain rate state, i.e. the fluid is described by a generalized Newtonian constitutive equation (not necessarily a Newtonian fluid per se). Because the geometry dictates that the only non-zero deformation rate components are the normal components, and further that the deformation rate components are not a function of position; it follows that the only non-zero stress components are the normal components, and that the stress components are not a function of position. Thus, ∇·τ= 0.
2. The fluid is incompressible. Therefore, ∇·v=0.
3. The system is isothermal. Therefore, ∇·q=0.
4. The flow is steady as a function of time. Therefore, $$\frac{\partial}{\partial t} = 0.$$

5. Inertial terms are negligible, so that v·∇v=0, and $$\nabla\left(\frac{v^2}{2}\right) = 0.$$

Using these assumptions, the momentum balance equation implies that the body force g is equal to ∇ p; i.e. in cylindrical coordinates $$g_z = \frac{\partial P}{\partial z} \text{ and } g_r = \frac{\partial P}{\partial r},$$

and in Cartesian coordinates $$g_z = \frac{\partial P}{\partial z} \text{ and } g_x = \frac{\partial P}{\partial x}.$$

However, even though (as discussed below) the assumption is inappropriate here, if one made the usual assumption that the body force g is attributable solely to gravity and is therefore negligible, coupled with the above assumptions, then it would follow that the pressure gradients would be zero—a conclusion that is clearly incorrect. Alternately, if it were assumed that the inertial terms are not negligible, then pressure gradients in the two geometries for the slit and semi-hyperbolic geometries would be, respectively:

$$P = P_{00} - \frac{\rho\dot{\epsilon}^2}{2}(z^2 + x^2) \text{ and } P = P_{00} - \frac{\rho\dot{\epsilon}^2}{2}\left(z^2 + \frac{r^2}{4}\right).$$

However, there are still two difficulties with these conclusions. First, the pressure gradients calculated using actual velocities were three to four orders of magnitude lower than the observed values. Second, the inferred pressure gradients were independent of the characteristics of the particular fluid.

Thus, the above-calculated pressure gradients cannot be correct, and the assumptions underlying their derivation must be re-examined.

Inertial forces may still be neglected as inconsequential. However, the various body forces represented by should be included. It was concluded that the body forces represented by g primarily represent not gravitational forces, but rather the resistance of the fluid to imposed orientation. This resistance to orientation causes the pressure gradient necessary to maintain $\dot{\epsilon}$ (which is also affected by the die geometry and the imposed volumetric flow rate). As fluid flows through the die, it is transformed from an isotropic liquid (melt or solution) to an oriented liquid, with the degree of orientation being dependent on the flow behavior. The pressure should be directly proportional to the potential function $\Phi$. Since pressure is the driving force, P is proportional to $\rho\dot{\epsilon}\Phi$, and may be expressed as:

$$P = A\Phi + B$$

where in Cartesian coordinates $$A = \frac{2P_0}{\dot{\epsilon}(x_0^2 - x_e^2 + L^2)} \text{ and } B = \frac{P_0(L^2 - x_e^2)}{\dot{\epsilon}(x_0^2 - x_e^2 + L^2)},$$

and in cylindrical coordinates $$A = \frac{2P_0}{\dot{\epsilon}\left(\frac{r_0^2}{2} - \frac{r_e^2}{2} + L^2\right)} \text{ and } B = \frac{P_0\left(L^2 - \frac{r_e^2}{2}\right)}{\dot{\epsilon}\left(\frac{r_0^2}{2} - \frac{r_e^2}{2} + L^2\right)}.$$

The variables $r_o$ and $r_e$ denote the entrance and exit radius values, respectively; $x_o$ and $x_e$ denote the corresponding half slit heights; and L denotes the centerline length of the die.

The stress term in the energy balance equation is $$\tau:\nabla v = \frac{3}{2}\tau_{zz}\dot{\epsilon}$$

for cylindrical coordinates, and for Cartesian coordinates is $\tau:\nabla v = 2\tau_{zz}\dot{\epsilon}$.

Under the above assumptions, the other two possibly non-zero terms in the energy balance are $$\rho\frac{D}{Dt}(\hat{H}) \text{ and } \frac{DP}{Dt}.$$

With the steady flow assumption these terms become $v\cdot\nabla\hat{H}$ and $v\cdot\nabla P$. In cylindrical coordinates, $$v\cdot\nabla P = v_r\frac{\partial P}{\partial r} + v_z\frac{\partial P}{\partial z}.$$

The effect of these relations may be found by realizing that P is directly proportional to $\Phi$, and integrating from r=0 to $r_i$ (where $r_i$ is the value of r at the interface either between the polymer and the die wall in skinless flow, or between the polymer and the skin in lubricated flow; $r_i$ is a function of z, although r is not a function of z), and then integrating from z=0 to L. The first term is proportional to $r_e^2$, and the second term is proportional to $L^2$. (The first term is negligible, as it is three orders of magnitude smaller than the second). The same result is obtained in Cartesian coordinates. In cylindrical coordinates, $$v\cdot\nabla\hat{H} = v_r\frac{\partial\hat{H}}{\partial r} + v_z\frac{\partial\hat{H}}{\partial z}.$$

By doing a similar double integration, it follows that the value of $v_r$ is two orders of magnitude smaller than $v_z$. Furthermore, $$\frac{\partial\hat{H}}{\partial r}$$

is significantly smaller than $$\frac{\partial\hat{H}}{\partial z}$$

because these terms are related to the temperature gradients and the phase change gradients. The die temperature is maintained at the melt temperature, and the melt exits the die into a lower temperature region. Therefore, the temperature gradient in the transverse direction is small, and (at least near the exit of the die) a larger gradient can occur in the longitudinal direction. Furthermore, the phase change occurs progressively in the longitudinal direction due to flow-induced orientation in that direction. Therefore, the enthalpy gradient in the transverse direction should be small, probably much smaller than the enthalpy gradient in the longitudinal direction. The same results are obtained for the pressure and enthalpy terms in Cartesian coordinates. With these simplifications, the energy balance expressed in terms of enthalpy can be integrated from the entrance to the exit, recognizing that the Hencky strain is $$\epsilon_h = \ln\left(\frac{A_0}{A_{ex}}\right) = \ln\left(\frac{r_0^2}{r_e^2}\right) = \ln\left(\frac{L}{z_0}\right)$$

Therefore, the stress component in cylindrical coordinates is $$\tau_{zz} = -\frac{2}{3}\frac{\Delta P}{\epsilon_h} + \frac{2}{3}\frac{\rho\Delta\hat{H}}{\epsilon_h}.$$

In Cartesian coordinates, this term is $$\tau_{zz} = -\frac{1}{2}\frac{\Delta P}{\epsilon_h} + \frac{1}{2}\frac{\rho\Delta\hat{H}}{\epsilon_h}.$$

The elongational viscosity term, $\eta_e$, in cylindrical coordinates is:

$$\eta_e = \frac{\tau_{zz} - \tau_{rr}}{\dot{\epsilon}} = \frac{3}{2}\frac{\tau_{zz}}{\dot{\epsilon}}$$

and in Cartesian coordinates is:

$$\eta_e = \frac{\tau_{zz} - \tau_{rr}}{\dot{\epsilon}} = 2\frac{\tau_{zz}}{\dot{\epsilon}}.$$

Note that in both Cartesian and cylindrical coordinates the elongational viscosity is:

$$\eta_e = -\frac{\Delta P}{\dot{\epsilon}\epsilon_h} + \frac{\rho\Delta\hat{H}}{\dot{\epsilon}\epsilon_h}$$

$$= -\frac{\Delta P A_{ex} L}{Q\epsilon_h} + \frac{\rho A_{ex} L \Delta\hat{H}}{Q\epsilon_h}$$

$$= -\frac{\Delta P L}{v_o \epsilon_h \exp(\epsilon_h)} + \frac{\rho L \Delta\hat{H}}{v_o \epsilon_h \exp(\epsilon_h)}$$

where $A_{ex}$ is the exit area, L is the centerline length of the die, Q is the volumetric flow rate, and $v_o$ is the initial velocity. The enthalpy term in essence represents a phase change (either stable or metastable), which may be progressively induced by the orientation imposed on the polymer melt or solution.

Experimental Results and Analysis of Converging Die Flows

Elongational viscosities and other properties were measured for two test systems, namely polyethylene-lubricated polypropylene, and "skinless" polypropylene, each using two different semi-hyperbolically converging conical dies having Hencky strains, $\epsilon_h$, of 6 and 7, respectively. The force g associated with imposing orientation was sufficiently large that we found, surprisingly, that the presence or absence of a lubricating skin layer was insignificant in determining flow characteristics. Development of a high Trouton ratio—on the order of 100 or more—reflects enthalpic and entropic contributions to developing orientation as the polymer melt or solution was transformed from an isotropic liquid to an oriented and highly non-isotropic liquid, perhaps even to an ordered or liquid crystalline state.

If it is assumed that the enthalpic term in the stress difference equations is included in an effective stress difference, $(\tau_{zz})_{ef}$ (mathematically equivalent to setting the enthalpic term to zero), then the effective elongational viscosity is:

$$\eta_{ef} = \frac{\Delta P}{\dot{\epsilon}\epsilon_h} = \frac{A_{ex} L \Delta P}{Q\epsilon_h} = \frac{L\Delta P}{v_o \epsilon_h \exp(\epsilon_h)}$$

This $\eta_{ef}$ reflects both the elongational deformation and the developing orientation. Therefore, if significant orientation develops in elongational flows, the uncorrected measured elongational viscosity is not a true measure of viscosity, but is still related to $\eta_{ef}$.

To appreciate the contribution of orientation development to entropic effects, the proximity of ambient conditions to a first order transition such as the melting point or a transformation to a liquid crystalline state needs to be considered. Polypropylene measurements were made at 200° C. at pressures of 1.15 MPa (11.5 atm) to 42.6 MPa (426 atm), and at strain rates of 0.02 to 136 s$^{-1}$ in the semi-hyperbolically converging conical dies; and at 6.05 MPa (60.5 atm) to 8.23 MPa (82.3 atm), and at strain rates of 0.1 to 0.4 s$^{-1}$ in the hyperbolically converging slit die. These conditions should be compared with those of transition phenomena. The peak melting point of the same polymer, as measured by differential scanning calorimetry in an isotropic, quiescent melt at atmospheric pressure, was 170° C. The last trace of crystallinity disappeared at 180° C. The dilatometric measured atmospheric melting point has previously been reported to be 174° C. The atmospheric pressure equilibrium melting point, obtained by extrapolating the last trace of crystallinity as a function of crystallization temperature, has previously been reported as 191° C. A dilatometric melting point at 300 atm of 191° C. has previously been reported; with a correction comparable to the difference between the measured and equilibrium melting points at atmospheric pressure, this measurement would correspond to an equilibrium melting point of 208° C. After considering these measured and reported transition temperatures, we conclude that the converging flow measurements were made very close to the equilibrium melting point.

At the equilibrium melting point, the free energy change $\Delta F$ between the melt state and an ordered state is zero. $\Delta F = \Delta H - T\Delta S$, where $\Delta H$ is the enthalpy change per unit volume (i.e., $\Delta H = \rho \Delta \hat{H}$) and $\Delta S$ is the entropy change per unit volume. Therefore, at the equilibrium melting point $\Delta S_f = \Delta H_f / T_m$, where $\Delta H_f$ is the enthalpy of fusion, $\Delta S_f$ is the entropy of fusion, and $T_m$ is the melting point. The latent heat (enthalpy change) of fusion for polypropylene has been reported as $2.15 \times 10^8$ J/m$^3$ (1 J/m$^3$=1 N/M$^2$=1 Pa) or 215 MPa ($2.15 \times 10^3$ atm). Therefore, the measured pressure drops of 1.15 MPa to 31.6 MPa for polypropylene in the converging dies ranged from 0.5% to 19.8% of the mechanical equivalent of the latent heat of fusion. (Enthalpy changes for transitions from isotropic liquid to liquid crystal are typically a fraction of the enthalpy of melting or crystallization, around this order of magnitude.) By assuming that the operating temperature of 200° C. (473° K) was the equilibrium melting point, and that the free energy change was zero, the measured pressure drops correspond to entropy changes of 2.43 kPa/° K (1 kPa/° K=1 J/(m$^3$-° K)) to 90.0 kPa/° K, compared to 455 kPa/° K for the melting of polypropylene.

The semi-hyperbolically converging dies were used to induce a constant elongational strain rate, and the extrudate was not cooled prior to exiting from the die—both conditions that differ from work previously reported from our laboratory. In polymer melt and solution rheology, it has previously been generally assumed that the material starts in an isotropic state, and that this state does not change much during and after flow. It has been discovered that these assumptions may not be justified in many polymer processing operations. The entropic and enthalpic changes noted above are indicative of orientation development. The effective elongational viscosity, measured at the processing elongational strain rates, suggests that similar orientation may develop unrecognized in many other polymer processing operations, but (depending on conditions) the orientation may fully or partially relax prior to solidification as extrudates swell after exiting a confined flow region. Thus, the effective elongational viscosity may be a useful measurement of the behavior of polymer melts in processes whose elongational flow field is less well-defined, and also in those having some elongational flow in a mixed flow field. Therefore, even though the measured value of the effective elongational viscosity is not a pure rheological property, it is useful in evaluating related processing behavior and resulting effects, including for example orientation development, swelling, residual stress, and crystallization behavior.

The figure compares elongational viscosity measurements made with and without a lubricating low-viscosity skin layer. As seen in the figure, body forces related to orientation development predominated over shearing effects due to the rigid boundaries. The net result was that elongational viscosities measured without a lubricating skin layer were, within limits of experimental error, identical to the elongational viscosities measured with the lubricating layer.

Deriving the enthalpy change in such processes is an important advance over prior methods. The enthalpy change may be estimated from the difference between the Trouton ratio-estimated contribution to the pressure drop and the actual pressure drop. The difference is an estimate of the enthalpy change contribution. With a high Trouton ratio, for example with a melt (e.g. polypropylene has values between 50 and 60, and our lyocell solutions have values ranging from about 3 to about 25), the enthalpy change dominates, and the imposed pressure drop is approximately equal to the enthalpy change per unit volume. (Note that enthalpy per unit mass is multiplied by density to obtain enthalpy per unit volume). This estimated enthalpy change is that associated with transformation to a metastable liquid crystalline form that will revert back to the stable, nearly isotropic form when elongational flow ceases. This method of estimating enthalpy changes is superior to static tests in which a metastable form is not induced, and in which no enthalpy change therefore occurs.

To estimate entropy changes, where a system is in thermodynamic equilibrium, e.g. at the equilibrium melting point, the entropy change is the enthalpy change divided by the absolute temperature. Even though elongational flow, does not represent thermodynamic equilibrium, this relationship between entropy and enthalpy is still approximately valid.

Obtaining the enthalpy by this process is similar in principal to the more conventional method of integrating under the curve in differential scanning calorimetry, but is based on measurements not obtainable by conventional differential scanning calorimetric techniques. One thereby obtains the latent heat of transformation for a first order thermodynamic transition (e.g. crystallization, melting, liquid crystal to melt, melt to liquid crystal, liquid crystal to liquid crystal, etc.) Furthermore, the measurement gives information on the quantitative effect of developing orientation. At a transition temperature, a change in enthalpy does cause a change in temperature (a condition that may also be satisfied by metastable transitions, e.g., those induced by flow); the change in enthalpy is then directly proportional to the change in entropy, and can therefore give a quantitative indication of the degree of orientation developed, in addition to resistance to orientation. Such measurements may be used to characterize polymer melts and solutions under flow conditions, which is difficult to accomplish by conventional thermal analysis techniques.

Thus, a method of estimating enthalpy and entropy changes due to the development of orientation may be summarized as follows. Equation 1 below defines the actual elongational viscosity, $\eta_e$:

$$\eta_e = -\frac{\Delta P}{\dot{\epsilon}\epsilon_h} + \frac{\rho \Delta \hat{H}}{\dot{\epsilon}\epsilon_h} \tag{1}$$

$$= -\frac{\Delta P A_{ex} L}{Q\epsilon_h} + \frac{\rho A_{ex} L \Delta \hat{H}}{Q\epsilon_h}$$

$$= -\frac{\Delta P L}{v_o \epsilon_h \exp(\epsilon_h)} + \frac{\rho L \Delta \hat{H}}{v_o \epsilon_h \exp(\epsilon_h)}$$

Equation 2 below defines an effective viscosity, $\eta_{ef}$, which is calculated from the measured volumetric flow, pressure drop, and die geometry:

$$\eta_{ef} = \frac{\Delta P}{\dot{\epsilon}\epsilon_h} = \frac{A_{ex} L \Delta P}{Q \epsilon_h} = \frac{L \Delta P}{v_o \epsilon_h \exp(\epsilon_h)} \tag{2}$$

Assumptions or approximations made to calculate $\Delta \hat{H}$ and $\Delta S$ from these two equations are the following:

(1) That $(\eta_e/\eta_s)=3$, where $\eta_s$ is the shearing viscosity, (which could be measured in a shearing flow rheometer, e.g., a capillary rheometer with a cylindrical capillary). This ratio, the Trouton ratio, is 3 for a Newtonian fluid. By assuming that the Trouton ratio is 3, one in effect assumes that all non-Newtonian and visco-elastic effects exhibited by the fluid are due to resistance to orientation.

(2) That the fluid is in equilibrium, i.e. $\Delta F=0$. Therefore, since $\Delta F=\Delta H - T\Delta S$, it follows that $\Delta S=(\Delta H/T)$, where T is the absolute temperature.

Thus, the enthalpy and entropy changes may be estimated as follows:

(a) Measure $\eta_s$ with a shearing flow rheometer (b) Measure $\Delta P$ and $Q$ for a given semi-hyperbolic die (so that L, Q, $A_{ex}$, and $\epsilon_h$ are known)

(c) Assume $(\eta_e/\eta_s)=3$, and calculate $\eta_e$ (Note that if the ratio $\eta_{ef}/\eta_s$ is close to 3, then the final calculated $\Delta H$ and $\Delta S$ will be near zero). This ratio $\eta_{ef}/\theta_s$ is referred to as the (measured) Trouton ratio, $T_R$.

(d) All of the terms in the second form of equation 1 are now known, except $\Delta \hat{H}$. Therefore, using this equation, one may calculate $\Delta \hat{H}$.

(e) Multiply the calculated $\Delta \hat{H}$ by $\rho$ to get $\Delta H$.

(f) Calculate $\Delta S$ using assumption (b) and the measured temperature on an absolute scale.

These steps may be simplified to the two relations:

$$\eta_{ef} = -\frac{\Delta P}{\dot{\epsilon}\epsilon_h}$$

$$\Delta H = \dot{\epsilon}\epsilon_h(3\eta_s - \eta_{ef})$$

or $$\Delta H = 3\eta_s \dot{\epsilon}\epsilon_h + \Delta P$$

EXAMPLES

Data from the flow behavior of polypropylene, and of 17% cellulose in an NNMO•H$_2$O solution, illustrate the calculation of these thermodynamic properties. For polypropylene at 200° C. the enthalpy change for the flow induced transformation to a metastable state ranged from $-0.53 \times 10^7$ to $-3.85 \times 10^7$ J/m$^3$, with an increase in magnitude as $\epsilon$ increased from 1.1 s$^{-1}$ to 128 s$^{-1}$, and with higher values for $\epsilon_h=7$ than for $\epsilon_h=6$. These values may be compared to the enthalpy of melting for polypropylene, $-2.15 \times 10^8$ J/m$^3$, which is expected to have a greater magnitude because the solid crystalline state has a much higher degree of organization than does a low order liquid crystalline form. The same trends were noted for the calculated entropy changes for polypropylene, which ranged from $-1.1 \times 10^4$ to $-8.13 \times 10^4$ J/(K m$^3$).

The data for the 17% cellulose solution in NMMO•H$_2$O at 95° C. were comparable, with the same trends observed.

The enthalpy change for this cellulose solution, corrected for concentration, ranged from $-1.99\times10^7$ to $-4.38\times10^7$ J/m$^3$, with an increase in magnitude as $\epsilon$ increased from 34.1 s$^{-1}$ to 94.0 s$^{-1}$, and with higher values for $\epsilon_h=7$ than for $\epsilon_h=6$. The entropy ranged from $-4.49\times10^4$ to $-11.9\times10^4$ J/(K m$^3$). These cellulose values are comparable to results for the same solution measured in a differential scanning calorimeter; the measured enthalpy and calculated entropy changes were $-0.441\times10^6$ to $-4.38\times10^7$ J/m$^3$, and $-1.20\times10^4$ to $-7.19\times10^4$ J/(K m$^3$), respectively.

These measurements demonstrated that, as expected, a higher degree of order was imposed on the polymers by the flow.

Miscellaneous

The complete disclosures of all references cited in this specification are hereby incorporated by reference. Also incorporated by reference is the complete disclosure of a commonly-owned United States patent application with the same filing date as this application: John R. Collier, Ioan I. Negulescu, and Billie J. Collier, "Cellulosic Microfibers," serial number 09/172,449, filed Oct. 14, 1998, now allowed with the issue fee paid. In the event of an otherwise irreconcilable conflict, however, the present specification shall control.

I claim:

1. A method for measuring the effective elongational viscosity $\eta_{ef}$ of a fluid, comprising the steps of:

(a) flowing the fluid through a die, at least a portion of which die comprises a semi-hyperbolic section, wherein said flowing is not lubricated, and whereby a pressure drop is induced in the fluid;

(b) measuring the pressure drop $\Delta P$ of the fluid as the fluid flows through the semi-hyperbolically shaped section; and (c) calculating the elongational viscosity $\eta_{ef}$ from a relationship equivalent to the form $$\eta_{ef} = [b-]a\left(\frac{\Delta PA_{ex}L}{Q\epsilon_h}\right)\underline{-b} = [b-]a\left(\frac{\Delta PL}{v_o\epsilon_h\exp(\epsilon_h)}\right)\underline{-b}$$

wherein a and b are constants, L is the centerline length of the semi-hyperbolically shaped section, $A_{ex}$ is the cross sectional area of the fluid as the fluid exits the semi-hyperbolically shaped section, $\Delta P$ is the pressure drop of the fluid in the semi-hyperbolically shaped section, Q is the volumetric flow rate of the fluid, $\epsilon_h$ is the Hencky strain in the die, and $v_o$ is the velocity of the fluid at the entrance to the die.

2. A method as recited in claim 1, wherein the fluid comprises a polymer melt, a polymer solution, or a food product.

3. A method for measuring the effective elongational viscosity $\eta_{ef}$ of a fluid, comprising the steps of:

(a) flowing the fluid through a die, at least a portion of which die converges hyperbolically in a first direction, while diverging in a perpendicular, second direction, wherein said flowing is not lubricated, and whereby a pressure drop is induced in the fluid;

(b) measuring the pressure drop $\Delta P$ of the fluid as the fluid flows through said portion of said die; and (c) calculating the elongational viscosity $\eta_{ef}$ from a relationship equivalent to the form $$\eta_{ef} = [b-]a\left(\frac{\Delta PA_{ex}L}{Q\epsilon_h}\right)\underline{-b} = [b-]a\left(\frac{\Delta PL}{v_o\epsilon_h\exp(\epsilon_h)}\right)\underline{-b}$$

wherein a and b are constants determined by the shape of the die, L is the centerline length of the said portion of said die, $A_{ex}$ is the cross sectional area of the fluid as the fluid exits said portion of said die, $\Delta P$ is the pressure drop of the fluid in said portion of said die, Q is the volumetric flow rate of the fluid, $\epsilon_h$ is the Hencky strain in the die, and $v_o$ is the velocity of the fluid at the entrance to the die.

4. A method as recited in claim 3, wherein the fluid comprises a polymer melt, a polymer solution, or a food product.

* * * * *